United States Patent
Prasser et al.

(10) Patent No.: US 7,085,344 B2
(45) Date of Patent: Aug. 1, 2006

(54) ARRANGEMENT FOR THE DETERMINATION BY MEASUREMENT OF A PROJECTION OF THE RADIATION ABSORPTION CAPACITY OF A PERIODICALLY-VARIABLE MEASURED OBJECT

(75) Inventors: Horst-Michael Prasser, Dresden (DE); Jochen Zschau, Dresden (DE)

(73) Assignee: Forschungszentrum Rossendorf E.V., Dresden (DE)

( * ) Notice: Subject to any disclaimer, the term of this patent is extended or adjusted under 35 U.S.C. 154(b) by 239 days.

(21) Appl. No.: 10/473,228

(22) PCT Filed: Apr. 4, 2002

(86) PCT No.: PCT/DE02/01217

§ 371 (c)(1),
(2), (4) Date: Apr. 14, 2004

(87) PCT Pub. No.: WO02/080772

PCT Pub. Date: Oct. 17, 2002

(65) Prior Publication Data

US 2004/0156470 A1    Aug. 12, 2004

(30) Foreign Application Priority Data

Apr. 7, 2001    (DE) ................ 101 17 569

(51) Int. Cl.
*H05G 1/60*    (2006.01)
(52) U.S. Cl. ............... 378/19; 378/98.8; 250/370.09
(58) Field of Classification Search ............. 378/8, 378/19, 51, 95, 98.8, 114, 116; 250/370.09
See application file for complete search history.

(56) References Cited

U.S. PATENT DOCUMENTS

| | | | | |
|---|---|---|---|---|
| 4,504,962 | A | * 3/1985 | Moore | 378/19 |
| 4,585,008 | A | 4/1986 | Jarkewicz | |
| 4,747,117 | A | * 5/1988 | Albrecht et al. | 378/19 |
| 4,817,119 | A | * 3/1989 | Ledley et al. | 378/19 |
| 5,668,375 | A | * 9/1997 | Petrick et al. | 378/98.8 |

FOREIGN PATENT DOCUMENTS

EP    1013225 A1 *    6/2000

* cited by examiner

*Primary Examiner*—Edward J. Glick
*Assistant Examiner*—Chih-Cheng Glen Kao

(57) ABSTRACT

Apparatus for measuring and recording a time-varying radiation absorption profile of an object undergoing a change that causes such a variation, includes: a continuous radiation emission source; a plurality of radiation detectors; a signal-reversing switch, connected to the detectors; a plurality of signal integrators for each detector, the integrators for each detector being connected to their detector by the signal-reversing switch, with portions of the plurality of the integrators being combined in banks of integrators, such that the signal reversing switch simultaneously connects the detectors with only the integrators of one of the banks; a control unit, connected with the signal reversing switch, for switching the signal reversing switch; a pulse generator, connected to an input of the control unit; and a synchronous signal transmitter, connected to an input of the control unit, for resetting the signal reversing switch to the integrators of a first bank of integrators.

9 Claims, 2 Drawing Sheets

Figure 1:
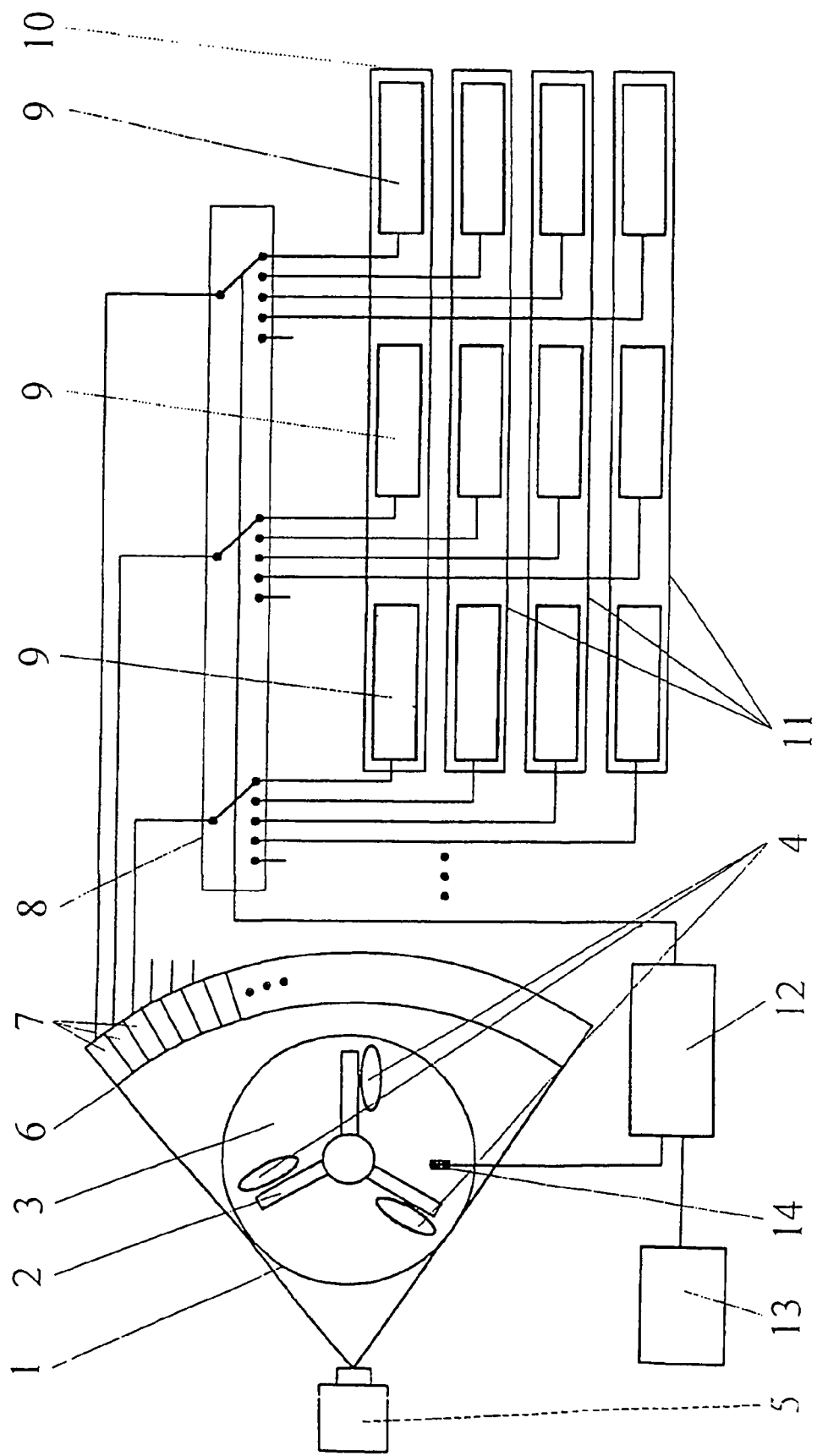

ARRANGEMENT FOR THE DETERMINATION BY MEASUREMENT OF A PROJECTION OF THE RADIATION ABSORPTION CAPACITY OF A PERIODICALLY-VARIABLE MEASURED OBJECT

This invention relates to an apparatus and method for measuring a projection of periodically variable radiation absorption characteristics of an object and for recording a profile of measured radiation absorption values. The apparatus is particularly applicable as a tomographic array apparatus for producing sectional images of objects, the shape or composition of which is subject to rapid changes, and especially wherein the changes are repeated periodically. Local differences in the attenuation behavior for ionizing radiation within the object are utilized for the imaging.

Tomography with ionizing radiation, generally X-ray or gamma radiation, is a method widely used in medicine and technology. For this purpose, the object is irradiated with quanta, which emanate from a practically point-shaped source of radiation. The intensity of the radiation, which passes through the object, is measured on the side opposite to the source with the help of a detector. The signal of a single detector provides a measure of the attenuation of the radiation by the object, which arises from the integral of the distribution of the absorption behavior along a line connecting the source and the respective detector. The signals from a multiple of detectors of an array represent a projection of the distribution of the attenuation characteristics and profile of the object in the direction of spread of the radiation beam. By changing the position of the source and the detector array, a number of independent projections of the distribution are obtained from different viewing directions. From these projections, the distribution of the attenuation characteristics of the object, from which conclusions concerning the structure and composition of the interior of the object, can be reconstructed with the help of numerical reconstruction methods.

Typically, a tomography aparatus uses an X-ray tube with the smallest possible focal point or an approximately point-shaped gamma source for generating a fan-shaped beam, which passes through the object in a fixed plane. On the opposite side, there is an arc of a number of radiation detectors, which are disposed next to one another in a plane. The detectors in this embodiment provide a one-dimensional projection of the two-dimensional attenuation profile of the object in the sectional plane, the so-called image plane, which is formed by the fan-shaped beam. In most cases, including also medical applications, the source and detector arc are rotatably positioned about the object in the image plane, in order to obtain projections from as many different directions as possible. From this, the two-dimensional attenuation profile in the image plane is determined by using tomographic image reconstruction methods.

For stationary tomography arrangements, it is also state of the art to rotatably position the object. This method is used to investigate technical objects. The determination of the distribution of liquid in a trickling filter with such an arrangement is described in D. Schmitz, N. Reinecke, G. Petrisch, and D. Mewes—X-ray Computed Tomography for Stationary Multiphase Flow in Random and Structured Packings, Proc. Frontiers in Industrial Process Tomography, Dec. 4 to 9, 1997, proc. pages 303–308.

Tomography arrangements are also known, for which a conical beam is used, which, after penetrating the object, is detected by a two-dimensional array of detectors (I. Tiseanu, M. Simon: High Resolution Cone-Beam Tomography for Two-Phase Flow Diagnostics, $2^{nd}$ International Symposium on Two-Phase Flow Modeling and Experimentation, Pisa, Italy, May 23–26, 1999, Proceedings pp, 1485–1492). In this case, a two-dimensional projection of the three-dimensional absorption distribution in the object is determined in one step. The projections, which are obtained by rotating the array about the object, can be used to reconstruct a spatial image of the object.

Because of the quantum character of the radiation, the accuracy of the measurement depends on the number of quanta recorded at the respective detector. The standard deviation of the intensity measurement is directly proportional to the square root of the number of the quanta recorded, the number of quanta increasing linearly with the time of measurement. Typically, a measurement time of the order of a few seconds to a few minutes per projection is required for producing projections with a measurement accuracy necessary for a subsequent reconstruction of an image. The measurement time can be reduced only by using more intensive sources, which leads to radiation-protection problems in the case of gamma tomography. However, gamma tomography is of importance particularly where larger objects, which are more difficult to penetrate, such as metallic components, are to be irradiated, since higher radiation energies and, with that, a better penetration, can be achieved more easily and less expensively with gamma sources than with X-ray sources.

For the reasons mentioned, the gamma or X-ray tomographic observation of processes in industrial targets, which takes place rapidly and which objects generally are difficult to penetrate by radiation, is not possible. Only if X-ray radiation is used, are tomography arrangements known, which permit a chronologically high-resolution observation to be made, because the high radiation intensity of the X-ray source, in combination with the electronic controllability of the electron beam, which is employed to produce continuous X-ray radiation, enables the required amount of projections to be obtained in the shortest time. Such a tomograph is described by D. P. Boyd, J. L. Couch, S. A. Napel, K. R. Peschmann, and R. E. Rand in Ultra Cine CT for Cardiac Imaging: Where Have We Been? What lies ahead? American Journal of Cardiac Imaging, 1 (1987) 2, pp. 175–185). For this arrangement, developed in cardiology for investigating rapid processes, the electron beam is passed with the help of deflection coils over an angle of 210° onto a tungsten target ring around the patient and thus produces a rotating fan of X-ray radiation, the intensity of which, after passing through the patient, is recorded by a stationary ring of 864 scintillator/photodiode channels. The equipment is operated with an accelerating voltage of 130 kV and makes amperages up to 640 mA possible. With the tomograph, produced according to this concept by the IMATRON Company, scanning times of 50 ms for an image plus an 8 ms interval between two scans can be achieved. It is the fastest commercial equipment presently known.

Even higher time resolutions are achieved by arrangements, for which the rotation of the projection direction is achieved by the sequential triggering of a number of X-ray tubes, which are disposed around the object. Such an arrangement with 18 pulsable X-ray tubes was described by M. Misawa, N. Ichikawa, M. Akai, K. Hori, K. Tamura, and G. Matsui in Ultra Fast X-ray CT Systems for Measurement of Dynamic Events in Two-Phase Flow, Advances in Thermal Hydraulics (Proc. ICONES), 1998. With this equipment, the gas content distribution in a two-phase current of water and air can be determined in a vertical pipeline with an approximately 50 mm diameter with a time resolution of 4 ms, so that individual gas bubbles become visible. All 18 X-ray tubes are triggered briefly, one after the other, within this time span. For this purpose, the tubes have a control electrode, which is located between the cathode and the anode. A further such tomograph is described by K. Hori, T. Fujimoto, K. Kawanishi and H. Nishikawa in Advanced High Speed X-ray CT Scanner for Measurement and Visualization of Multi-Phase Flow, 0ECD/CSNI Specialist Meeting, Santa Barbara, Calif., 1997. For this equipment, 66 X-ray sources are used. The measurement time for determining a distribution is 0.5 ms. For both arrangements, the energy of the radiation is below 150 keV. This excludes use with larger objects of more highly absorbing materials, such as metallic materials.

The use of gamma sources with correspondingly higher radiation energy, which are therefore most suitable for objects that absorb more strongly, does not, however, permit the source to be controlled in the desired manner. For gamma tomographs, the only possibility for changing the projection direction is through the mechanical rotation of the source and detector or by encircling of the object with the source using a stationary ring of detectors. It is not possible to pulse the source or to affect it with electric or magnetic fields so as to obtain projections from different viewing directions or to deflect the beam. With scanning times of a few seconds, mechanical systems have limits. A known tomograph for two-phase currents, the time resolution of which reaches the second range, works with a gamma source, which circles the object in 2 seconds, while a ring of detectors is stationary (A. C. De Vuono, P. A. Schlosser, F. A. Kulacki and P. Munshi—Design of an Isotopic CT Scanner for Two-phase Flow Measurements—IEEE Transactions on Nuclear Science, vol. NS-27, No. 1, February 1980). The alternative variation of using several stationary sources (T. Froystein—Flow Imaging by Gamma-ray Tomography: Data Processing and Reconstruction Techniques, Systems—Proc. Frontiers in Industrial Process Tomography II, Apr. 8–12, 1997, Delft (Netherlands), 185–187) has the disadvantage that only a small number of projections can be obtained, since otherwise the individual fan-shaped beams would overlap. Because of that, the quality of the achievable image reconstruction is slight and the spatial resolution is unsatisfactory.

It is an object of the invention to present an arrangement, which permits, even in the case of objects having a configuration or composition which is subject to rapid, periodically repeating changes, the determination of projections, which represent an instantaneous condition or a sequence of instantaneous conditions of the periodically changing distribution of the absorption behavior, from which the distribution profile itself can be reconstructed, the apparatus achieving this with a gamma source, which emits continuous radiation.

Pursuant to the invention, this objective is accomplished by an apparatus which includes a continuous radiation emission source, a plurality of detectors for the type of radiation being used, with the detectors being positioned behind the object being measured, relative to the source, with the detectors being connected over a signal reversing switch to a plurality of signal integrators per detector, which are combined in banks, wherein the reversing switch connects the detectors simultaneously with the integrators of one of the banks, and the signal reversing switch is connected to a control unit, the input of which is connected to a pulse generator, for switching the signal reversing switch, and the input of the control unit is connected with a synchronous signal transmitter for resetting the signal reversing switch to the signal integrators of the first bank. It is a feature of a tomograph according to the present invention that the detectors of the detector array are connected over a signal distributor with several banks of signal integrators. One signal integrator is assigned to each detector in each bank. The signal distributor always passes the signals of the detectors only to the signal integrators of one of the banks, commencing with the first bank. After a specified, constant time interval $t_B$, which is also referred to as the bank time, has elapsed, all detector signals are passed on to the next bank of signal integrators by a control unit, with which the signal distributor is connected. For the apparatus to function, a synchronous signal must be available, which appears after the complete period $t_p$ of chronological change of the object has elapsed. This synchronous signal is sent to the control unit and, at the conclusion of the period of change of the object, causes the control unit to switch back to the first bank of signal integrators and to commence the signal distribution process again. For performing measurements, the tomography apparatus, including source and detectors, is brought into a position, which corresponds to the projection that is to be determined. The signal integrators are reset in order to commence the subsequent integration at zero. After a predetermined number of N periods of change of the object, the measuring process is interrupted. The measurement information, present thereafter in each individual bank of signal integrators, represents the result of determining a projection in the measurement plane, which is specified by the set alignment of sources and the arrangement of detectors and in the specified direction, which is moreover assigned precisely to a time interval of duration $t_B$, which is generated by a particular bank number, and represents a section of the period $t_p$. In the bank designated by number i, there is a projection, which is assigned to the time interval $(i-1)t_B < t < it_B$. The effective measuring time $t_M$, which determines the statistical error of the values measured, arises from the number of periods P recorded and the time interval from $t_B$ to $t_M = Nt_B$. The statistical certainty of the values measured can be improved by increasing the number of periods of change of the object, over which the integration is carried out.

A generally known method is used for carrying out the tomographic measurement, wherein the source and detectors are rotated stepwise and the measuring process is repeated for each projection direction. Subsequently, when a tomographic image reconstruction is carried out with all projections, originating from a single time interval i, the desired distribution profile in the measurement plane for the time interval i is obtained. After the reconstruction for all available time intervals is carried out, the individual results are assembled into a sequence, which reproduces the periodically changing sectional image of the object. The number of time intervals, available for constructing the sequence, is given by the ratio $t_p/t_B$.

In the following, the invention is explained in greater detail in two examples. In the accompanying drawings, FIG. 1 shows a basic embodiment of the apparatus of the present invention; and FIG. 2 shows the apparatus of FIG. 1, supplemented by a computer for detecting the signals.

Both examples relate to an apparatus for the tomographic determination of the density distribution profile in the impeller of an axial pump, which is in the operating state and is pumping a mixture of a gas and a liquid. The interaction between the liquid-gas mixture and the impeller results in a characteristic distribution of the gas phase, which is reflected in a corresponding distribution of the density of the mixture. The absorption capability of the mixture for gamma radiation is proportional to the local density of the mixture. Because of the rotation of the pump impeller, the density distribution is subjected to periodic changes and the period $t_p$ coincides with the duration of one rotation of the impeller. In FIG. 1, the pump housing 1 is shown schematically in cross-section with the impeller 2. Regions, which are filled with the liquid phase 3 or the gas phase 4, are shown. The impeller is a screw-like construction with three blades and a diameter of 220 mm. In the sectional representation, there are three sectional areas of the impeller, extending radially from the shaft to the outside. The pump is irradiated with the gamma radiation emanating from the source 5 and emitted by the nuclide, cesium-137. The activity is 185 GBq and the energy is 662 keV. Due to the high radiation energy, it is possible to irradiate the pump housing 1 and the impeller 2 effectively.

Figure 2:
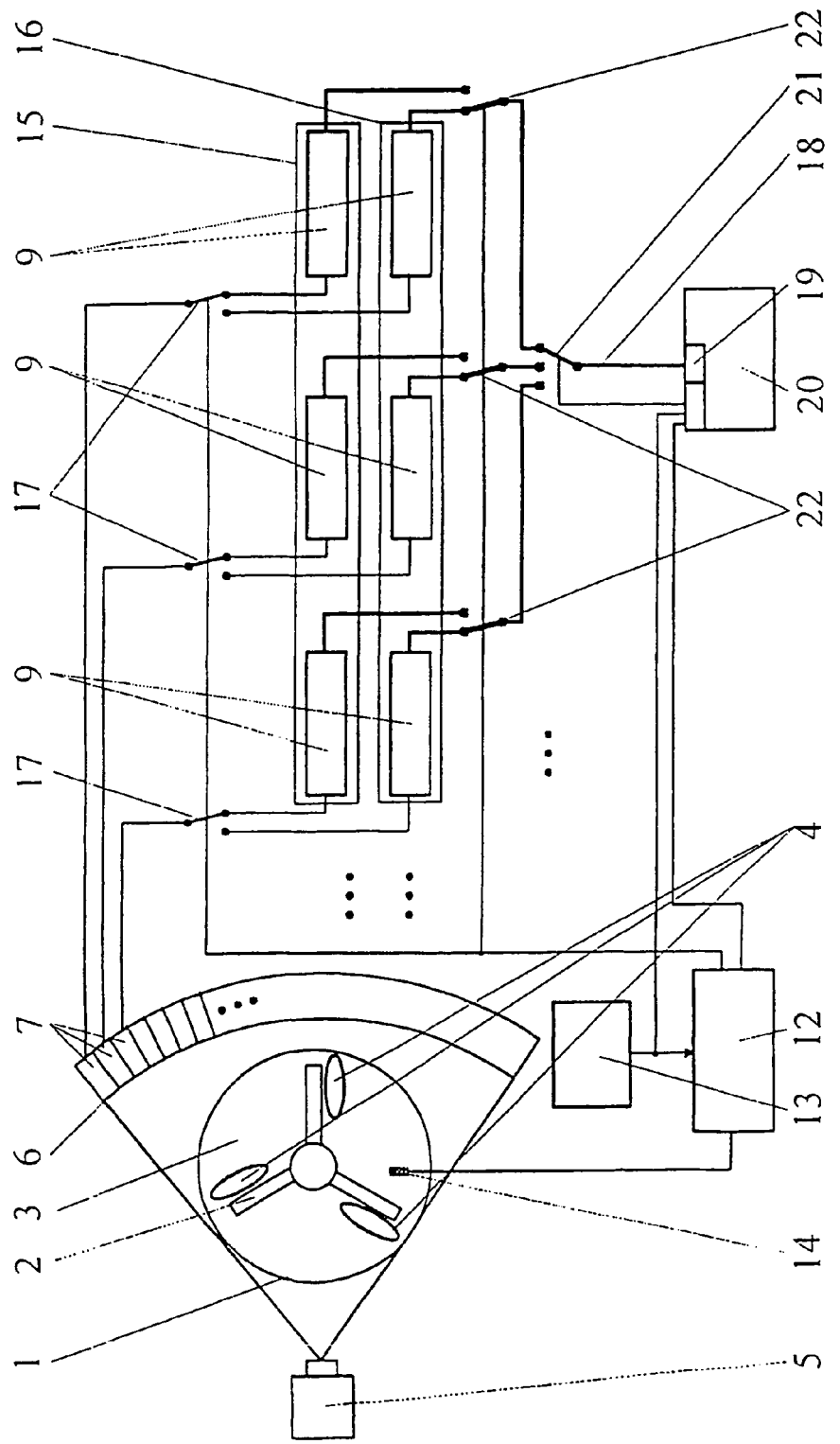

The first example, shown in FIG. 1, shows a determination of projections of the density distribution of the object measured for four consecutive brief time intervals having a duration of $t_B$. On the side opposite the source 5, there is an arc 6 of 64 individual detectors 7 for the gamma radiation. In the example, the detectors are scintillation crystals of bismuth germanate with optically coupled secondary electron multipliers and signal amplifiers with a pulse output, integrated in the arc 6 of detectors 7. The distance between the source 5 and the arc 6 of detectors 7 is 730 mm. The detector crystals have an end surface of 10×10 mm$^2$, which is aligned towards the source 5, and a length of 30 mm. The source 5 is equipped with a collimator for producing a fan-shaped beam, which is directed towards the arc 6 of detectors 7. The measurement plane, which is formed by the orientation of the arc 6 of detectors 7 and of the source collimator, intersects the pump housing 1 perpendicularly to the axis of rotation of the impeller 2. The periodically changing measurement object is formed by the medium being pumped, which is located in the image plane and consists of regions, which are filled either with gas 4 or with liquid 3, and by the cross-section through the rotating impeller 2 in the image plane, and through the pump housing 1.

The electrical pulses, which are produced by the gamma quanta arriving at the detector 7, are passed on to a signal-reversing switch 8, which connects each of the detectors 7 with a signal integrator 9. The signal integrators 9 are combined in a first bank 10 and three further banks 11. Only the first three of the 64 signal integrators 9, which are required for detecting the signals of the 64 detectors 7 present, are shown in FIG. 1. The presence of a continuation of the array for detecting the signals of the further detectors (not shown) is indicated by ellipsis. The number of counter banks 11 is changeable, as necessary. The total number of counter banks is denoted by the letter B. In the example of FIG. 1, B=4.

The signal integrators 9 of the example are binary counters, which digitally detect the gamma quanta recorded by the detector 7. The signal-reversing switch 8 connects the detectors at a given time only with the counters 9 of the associated bank 10 or 11. The switch position, shown in FIG. 1, corresponds to the start of the measurement, that is, the detectors 7 are connected with the counters 9 of the first bank 10. The signal distributor 8 is connected with the control unit 12, which causes the signal-reversing switch 8 to switch the signals of the detectors 7 after a specified time $t_B$ to the counter 9 of the subsequent bank of the other counter banks 11. For the purpose of controlling the timing, the control circuit 12 receives equidistant pulses from a clock pulse generator 13. After the fourth pulse of the clock pulse generator 13, the control unit 12 switches the signal-reversing switch 8 into the fifth switch position, which is not connected with the binary counter, as a result of which the counting process is interrupted. The control circuit 12 furthermore is connected with an angular momentum transmitter 14, which provides a pulse for each revolution of the impeller 2. These pulses arrive periodically at a time interval of $t_p$. When these pulses appear, the control circuit 12 switches the signal switch 8 back to the counter 9 of the first bank 10.

After a certain, specified number of revolutions of the impeller 2, the measuring process is stopped. The pulse numbers, totaled in the counters 9, correspond to the number of gamma quanta recorded by the respective detector 7, each counter 9 being assigned to only one detector 7 and, due to its association with one of the counter banks 10 or 11, a time interval also unambiguously fixed within the rotation period of the impeller 2. The information, stored in the respective counter bank 10 or 11 at the conclusion of the measurement, accordingly represents the projection of the distribution profile of the absorption of the measurement object in the measurement plane, formed by the fan-shaped beam, for a known time interval within the rotation period. Four chronologically consecutive time intervals can be evaluated with the number of counter banks 10 and 11, shown in FIG. 1.

The density distribution profile or the gas content distribution profile is determinable by generally known techniques and, by repeating the measurement process with stepwise rotation of the arrangement of source 5 and detector arc 6. A set of independent projections is recorded from the various viewing directions. From the set of projections, which originate from the same counter bank, the two-dimensional density distribution is determinable in the measurement plane for the time interval assigned to the counter bank by using tomographic reconstruction methods. In the present axial pump example, the time interval corresponds to a particular interval of the angle of rotation $\Phi$ of the impeller 2, the zero point of the angle of rotation being determined by the pulse of the angular momentum transmitter 14, which appears once during each revolution. For the number of the counter bank i, the angular interval is as follows: $(i-1) \times 360° \times t_B/t_p < \Phi < I \times 360° \times t_B/t_p$. With that, the reconstructed density distribution profile is also assigned to one specified rotational angle interval. The angular resolution is $\Delta\Phi = 360° \times t_B/t_p$.

The example relates to a pump, the impeller 2 of which rotates at about 1500 rpm. From this, the period of rotation $t_p$ is calculated to be 40 ms. An angular resolution of better than 1° is realized in the example, from which a bank time of approximately $t_B=0.1$ ms arises. In order to be able to determine the period of rotation of the impeller 2, the number of counter banks in the arrangement of FIG. 1 must be at least $t_p/t_B$, that is, at least to 400 for the values given. It corresponds to the number of angular steps, which are to be resolved. Accordingly, it is necessary to increase the number of counter banks from 4 to 400, if the complete determination of the whole period of revolution is to take place. For the 64 detectors employed in the example and the arrangement of FIG. 1, the total number of counter components is at least 400×64=25600. The second example, shown in FIG. 2 pertains to a way of reducing the circuitry for such an increased number of counter banks.

Compared to the example of FIG. 1, the apparatus of the second example further includes a data acquisition computer 20. In further comparison to the apparatus of FIG. 1, the number of counter banks is reduced to two counter banks 15 and 16. In FIG. 2, only the first three of 64 counters, which are assigned to the existing 64 detectors 7, are shown. Signal switches 17 reciprocally connect the two counter banks 15 and 16 with the associated detectors 7, so that at all times, only the counters of one of the two banks 15 or 16 determine the gamma quanta recorded at the detectors 7. The digital counter readings of those counters 9 of the bank, not connected with the detectors 7, are acquired over a data bus 18 and a parallel interface 19 by a data acquisition computer 20. The computer 20 controls the data acquisition by addressing a bus reversing switch 21, which is implemented by using bus driver circuits with a chip-select input. This bus-reversing switch 21 connects the output of the counters 9 of the selected bank, consecutively with the parallel interface 19 of the computer 20. The bank is switched-over between the counting and reading operation by the control unit 12, the reversing signal, as shown in FIG. 2, being passed parallel to the signal switches 17, to the bus switches 22 and to the data acquisition computer 20. The switch position, shown in FIG. 2, corresponds to the state when the counter 9 of the bank 15 detects the pulses of the detectors 7 and the counters 9 of the bank 16 are read sequentially by the computer 20.

The further summing of the counter results is accomplished by software in the data acquisition computer 20. In the memory of the computer, a data field is set up in the form of columns and rows of a data matrix. The number of columns is identical with the number of detectors 7 and the number of rows corresponds to the number of angular steps, which are to be resolved. The data, read sequentially from the counters 15 and 16, are added to the stored values of a row of the matrix. After exchanging counter banks 15 and 16, the computer 20 continues this summation with the next, subsequent line of the matrix. In addition, the computer 20 receives the pulses from the angular momentum transmitter 14, which indicate the completion of a complete revolution of the impeller 2. Upon arrival of one of these pulses, the summation is commenced once again at the first row of the data matrix. After a certain, specified number of revolutions of the impeller 2, the measuring process is stopped. Counter results, which correspond to the result obtained with the arrangement of FIG. 1, are then stored in the data matrix. At the same time, the expenditure for hardware is reduced, since only 2×64 counters are required.

The invention claimed is:

1. Apparatus for measuring and recording a time-varying radiation absorption profile of an object undergoing a change causing a time variation in said radiation absorption profile of said object, said apparatus comprising:
   a continuous radiation emission source;
   a plurality of detectors, capable of detecting radiation produced by said source, said detectors being positioned behind said object being measured, relative to said source;
   a signal reversing switch, connected to said detectors;
   a plurality of signal integrators for each said detector, said integrators for each said detector being connected to their respective detector by said signal reversing switch, with portions of said plurality of said integrators being combined in banks of integrators, such that said signal reversing switch simultaneously connects said detectors with only said integrators of one of said banks of integrators;
   a control unit, connected with said signal reversing switch, for switching the signal reversing switch;
   a pulse generator, connected to an input of said control unit; and
   a synchronous signal transmitter, connected to an input of said control unit, for resetting said signal reversing switch to said integrators of a first said bank of said integrators.

2. Apparatus according to claim 1, wherein said synchronous signal transmitter is a phase angle detector, to which a discriminator, in turn connected to a time-varying periodically changeable part of said object being measured, is connected in series.

3. Apparatus according to claim 1, wherein said detectors have a pulse output and said integrators are pulse counters.

4. Apparatus according to claim 1, wherein:
   said detectors are connected by said signal switch to two signal integrators per detector, said integrators being pulse counters that are integrated in two banks;
   said signal switch simultaneously connects said detectors with only said signal integrators of one of said two banks;
   digital outputs of said signal integrators are reciprocally connected by a data bus with a data-acquisition computer; and
   said signal switch and a bus reversing switch are connected to a common control unit.

5. Apparatus according to claim 1, wherein said detectors have an electrical analog output and said signal integrators are analog integrators.

6. Apparatus according to claim 1, wherein:
   said detectors are connected by said signal switch to two signal integrators per detector;
   said integrators are analog integrators, integrated in two banks;
   said signal switch simultaneously connects said detectors with only the analog integrators of one of said two banks;
   analog outputs of said analog integrators of said banks are each reciprocally connected by a digital analog converter and a bus reversing switch to a data bus with a data acquisition computer; and
   said signal switch and said bus reversing switch are connected to a common control unit.

7. Apparatus according to claim 1, further comprising a sensor, mounted on said object being measured; and wherein said pulse generator generates pulses at a plurality of fixed phases of said change in said object being measured, per period of change.

8. Apparatus according to claim 1, wherein said detectors are arrayed in a pattern selected from the group consisting of: linearly; and in an arc.

9. Apparatus according to claim 1, wherein said plurality of matrix.

* * * * *